United States Patent
Ferrão De Paiva Martins et al.

(10) Patent No.: US 8,377,699 B2
(45) Date of Patent: Feb. 19, 2013

(54) DETECTION AND QUANTIFICATION SYSTEM OF BIOLOGICAL, MATTER CONSTITUTED BY ONE OR MORE OPTICAL SENSORS AND ONE OR MORE LIGHT SOURCES, ASSOCIATED PROCESS AND RELATED APPLICATIONS

(75) Inventors: Rodrigo Ferrão De Paiva Martins, Charneca Da Caparica (PT); Pedro Miguel Ribeiro Viana Baptista, Lisbon (PT); Elvira Maria Correia Fortunato, Charneca Da Caparica (PT)

(73) Assignee: Universidade Nova de Lisboa, Lisbon (PT)

( * ) Notice: Subject to any disclaimer, the term of this patent is extended or adjusted under 35 U.S.C. 154(b) by 0 days.

(21) Appl. No.: 12/440,297

(22) PCT Filed: Sep. 7, 2007

(86) PCT No.: PCT/IB2007/053614
§ 371 (c)(1),
(2), (4) Date: Mar. 6, 2009

(87) PCT Pub. No.: WO2008/029374
PCT Pub. Date: Mar. 13, 2008

(65) Prior Publication Data
US 2010/0041161 A1   Feb. 18, 2010

(30) Foreign Application Priority Data
Sep. 8, 2006 (PT) .................................. 103561

(51) Int. Cl.
*G01N 33/00* (2006.01)
*G01N 21/00* (2006.01)
*G01N 21/25* (2006.01)
*G01N 33/68* (2006.01)

(52) U.S. Cl. ........... 436/86; 436/94; 436/91; 422/82.05; 422/68.1; 422/50; 422/82.09

(58) Field of Classification Search ............ 436/94, 436/91, 86; 422/82.05, 68.1, 50, 82.09
See application file for complete search history.

(56) References Cited

U.S. PATENT DOCUMENTS
2004/0110206 A1 * 6/2004 Wong et al. ................. 435/6
2005/0157301 A1   7/2005 Chediak et al.
2006/0127931 A1 * 6/2006 Schmidt et al. ............. 435/6

FOREIGN PATENT DOCUMENTS
WO   WO03/046527   6/2003

OTHER PUBLICATIONS

Storhoff, J. J., et al., "Gold nanoparticle-based detection of genomic DNA targets on microarrays using a novel optical detection system," Biosensors and Bioelectronics 2004;19:875-883.
Storhoff, J. J., et al., "Homogenous detection of unamplified genomic DNA sequences based on colorimetric scatter of gold nanoparticle probes," Nature Biotechnology Jul. 2004;22(7):883-887.
International Search Report for PCT Patent App. No. PCT/IB2007/053614 (Jul. 2, 2008).

* cited by examiner

*Primary Examiner* — Christine T Mui
(74) *Attorney, Agent, or Firm* — Kenealy Vaidya LLP

(57) ABSTRACT

The present invention relates to a system and process for detection and/or qualitative and quantitative identification of the biological material, such as specific sequences of nucleic acids or proteins as antibodies, present in biological samples. The system is composed by one or more light sources (1) combined with one or more integrated optical photo sensors, or not, and various electronic components (4), necessary for obtaining/processing of the signal emitted by the metal nanoprobes functionalized with a solution of biological composite, as well as also a micro-controller and a microprocessor, fixed or portable. This photosensor structure is able to detect and to quantify the color variations produced by metal nanoprobes, being this preferentially gold, functionalized by oligonucleotides complementary to specific DNA/RNA sequences, proteins, as for instance antibodies and/or antigens related with certain disease, or other sample or solution of biological composite, that are to be investigated. The detection and quantification process is based on the response of a photosensor, singular or integrated, based on thin film technology of amorphous, nanocrystalline or microcrystalline silicon and their alloys, as well as the new active ceramic semiconductors, amorphous and not amorphous.

20 Claims, 2 Drawing Sheets

Figure 1:
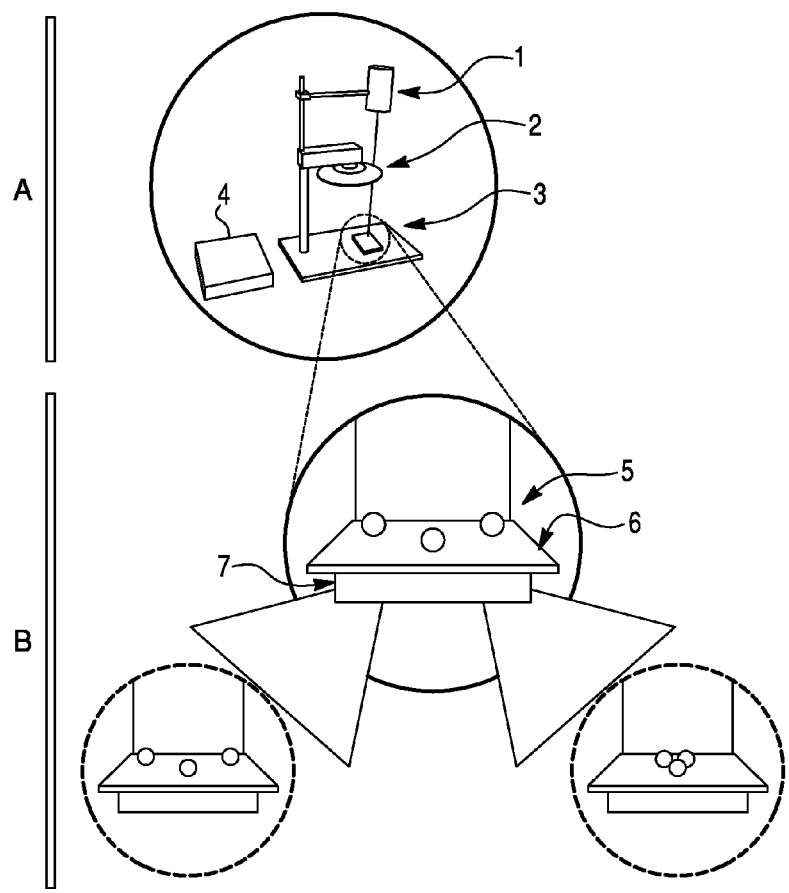

DETECTION AND QUANTIFICATION SYSTEM OF BIOLOGICAL, MATTER CONSTITUTED BY ONE OR MORE OPTICAL SENSORS AND ONE OR MORE LIGHT SOURCES, ASSOCIATED PROCESS AND RELATED APPLICATIONS

This application is a U.S. national phase filing under 35 U.S.C. §371 of PCT Application No. PCT/IB2007/053614, filed Sep. 7, 2008, and claims priority thereto under 35 U.S.C. §119 to Portuguese patent application no. 103561, filed Sep. 8, 2006, the entireties of both of which are incorporated by reference herein.

FIELD OF THE INVENTION

The present invention concerns to a new system and process able to analyse organic molecular samples or aqueous biological composite solutions based on calorimetric methods (detection, quantification and identification).

The system is constituted by a monochromatic, controllable, light source, optical sensor capable of detecting and quantifying the colorimetrical differences produced by solutions containing metal nanoprobes, preferentially gold.

These probes can be functionalized with specific oligonucleotides, complementary to DNA/RNA sequences, proteins, as for instance antibodies and/or antigens related with certain diseases, or other sample or solution of biological composite, and it can be applied in several areas of biotechnology, including biomedicine.

SUMMARY OF THE INVENTION

The present invention relates to a system and process for detection and/or qualitative and quantitative identification of a sample or aqueous solution of biological composite, as for instance specific sequences of nucleic acids present in biological samples, that when functionalized with metal nanoprobes, changes their absorption/emission range according to the chemical reactions.

The detection and quantification process is based on the response of a photosensor, singular or integrated, based on thin film technology of amorphous, nanocrystalline or microcrystalline silicon and their alloys, as well as the new active ceramic semi-conductors, amorphous and not amorphous, capable of optically detecting the absorbed/emitted light.

This photosensor structure detects and quantifies the colour variation, associated to a reference (signal of the light source). This colour variation is caused by metal nanoprobes, being this preferentially gold, when functionalized with the sample or aqueous solution of biological composite, as for instance oligonucleotides complementary to specific DNA/RNA sequences that are to be investigated.

The detection response corresponds to the difference between the reference values (light beam directly on the sensor) and the values after the introduction of the biological liquid.

This analogical signal is properly conditioned by the appropriate electronics and presented in analogical or digital form.

The resulting signal, through the appropriate choice of the calibration and correction algorithm, is proportional to the concentration of the biological sample functionalized to the probes.

The referred system and detection process and/or identification and quantification process resulting from the molecular analyses of the sample or aqueous solution of biological composite have application to biotechnology, including biomedicine, as for instance, in the quantification and detection of nucleic acids sequences present in a biological sample.

INVENTION BACKGROUND

Nowadays, in many clinical and laboratorial diagnostics of biological samples, simple low cost systems are required, with the possibility to quantify very small amounts in a fast and reliable way.

Among these, strong interest is put on the identification of nucleic acids, DNA/RNA, and/or proteins, for instance antibodies and/or antigens related with certain disease.

Nucleic acids are the genetic material of any living organism, containing specific information that allows its complete characterization. Therefore, it is possible to identify characteristic sequences for each living being, from which relevant information can be obtained: identification of sequences; identification of mutations which can cause diseases; detection of pathogenic agents such as bacteria and virus, etc [1].

Most of the known characterization techniques for DNA/RNA sequences are based on the selective and specific hybridization of a small oligonucleotide (probe) with the complementary DNA sequence (target). Nowadays, fluorescence or radioactive methods are the most used for the detection of specific sequences by hybridization. However, it is verified that these techniques are expensive and extremely slow [2, 3]. In addition, hybridization techniques need a significant amount of target to obtain a signal. Following this procedure these techniques are mainly susceptible to be applied after an amplification process of the nucleic acid from the sample in question, through the technique of polymerase chain reaction—PCR. PCR allows an amplification of the number of DNA molecules available, mimmetizing what happens in the multiplication process of cells in an organism.

New real time amplification techniques (for example Real-time PCR) offer a high automation level and decrease the time necessary for amplification and detection. With the use of these techniques, it is also possible to obtain quantitative results.

Nevertheless, in spite of the high costs associated with the equipment and for testing, these technologies present a great disadvantage, which prevents a broader use in laboratories—the sample handling, since highly purified samples are needed, which consequently requires highly specialized personal and equipped laboratories [4] [5].

More recently, DNA chips (micro-groups of integrated sensors) have earned some popularity. Their largest application has been in gene expression studies, where the chips offer simultaneous analyses of several genes for a single sample. Basically, this technique is based on simultaneous hybridization of a high number of samples with minimum amounts of sample.

In spite of all this, the amplification step is still required. Additionally, the chip content is still a problem to be solved, besides this to be a costly technology, since these chips are not reusable [6].

Several calorimetric methods for nucleic acids detection have been developed [7-10]. Some of these methods are based on the optical properties (plasmon surface resonance) of gold or other metal nanoparticles [11-12], function of their form and size.

These nanoparticles of gold or other metal, such as silver or silver-gold alloys, are extremely sensitive to the changes of the medium, presenting a colour variation, from red to blue in the case of gold. The colour variation can be the result of the aggregation of several particles, for instance, by the action of a non complementary DNA chain.

The colour change is a macroscopic response originated from a nanometric scale phenomenon, where DNA/RNA can behave in a complementary or non complementary manner. For each one of these reactions a different sensor system response exists for the absorption of incident light.

By doing so, the hybridization of DNA or RNA probes linked to particles of gold for the identification of specific sequences is a low cost and easy to use technique, which could be an alternative to conventional methods. Even though, the technique based on gold nanoparticles is quite simple and low cost one, it still requires the need to register the colour variation. Even more, if the target presents just a small colour change in relation to the probe, the deviation of the maximum (colour) peak can only be detected through equipment with a high sensitivity, involving also some limitations (such as the large amount of biological liquid required and the need of a high spectrum resolution).

On the other hand, besides the detection of the deviation in relation to the peak, these techniques are unable to supply quantified information, in terms of the intensity variation associated with one given colour or colour deviation.

Presently, there are several documents that describe related techniques in this area: so, the document corresponding to the patent US2006127931 refers to a detection process of the transmitted light associated to several nano-cavities. In this case the confinement of the light, associated to the areas where the nanoparticles are located, it is detected by measuring the reduction of the light transmitted through a photonic structure. This process is optimized for the range of wavelengths between 1450 and 1600 nanometers. The process of nano-cavities and wave guide is not considered in the present invention.

Patent document DE102004015272 is related to bio-sensors that use CMOS (complementary metal-oxide-semiconductor) technology which is intended to determine the presence of DNA that hybridizes with target molecules placed on the photodiode. By this way it is not possible to re-use the sensor, nor it is possible to quantify the signal, nor is it possible to determine the colour deviation. Even more, it does not use nanoprobes of metallic particles in the detection process. The probes/samples analysed are linked to an electrode which generates an electrical signal. The structure is different from the one proposed in this invention, since it is fully based on CMOS technology.

Patent document US2005046847 deals with a method for optical illumination and DNA detection considered of low cost and of fast response. The system is based on the sweeping of integrated groups of sensors based on micro-electromechanical systems. In this invention, the light sources to be used are multiple and commuted amongst themselves, so that the same bio-sensor can be illuminated by more than one light source, or a light source can illuminate several bio-sensors. Besides, it uses filters for discrimination of the different wavelengths and/or discrimination of the polarization of the light beam. Finally, it can still include micro-lenses to focus the incident light. However this technology does not apply to the nanoparticles component and it differs from the present invention on the following aspects: the optical properties of the sample in study have to be analyzed after optical illumination, therefore a post-processing/analyses of the sample is necessary. It is not present in the method the application of metal/gold nanoparticles. The structure is formed by two matrices, one containing the light sources and the other containing the detectors, therefore it is different to the present invention.

The document WO0075276 refers to a device for DNA detection based on a gallium arsenide sensor. In this case, the DNA probe is directly absorbed on the surface of an upper layer of the sensor, which it is a degenerated semiconductor conductive layer, or an insulating or semi-insulating layer. The detection is made by hybridization of the DNA with the sensor and controlled by the variation of the current after application of an electric field, or vice-versa. The material and structure used are also different. Therefore, this system is completely different from the proposed one because it is based on the change of conductivity of the medium.

The document DE10142691 claims a device for biochemical reaction detection and measurement by light transmission through pores of the reaction substrate. This invention uses porous silicon and detection by illumination and, for that reason it differs substantially from the invention claimed in the present document.

The document WO2004044549 presents methods and compositions for detection, in which a universal detector, containing probes, is incubated with marked molecules. This method makes use of markers but does not specify the detection method used (calorimetric, impedance, etc.).

The document EP0667398 describes methods and devices for detection of specific sequences of DNA without having to use chemical markers, using only hybridization techniques. The present invention differs from the published document since an automatic method for the detection of the hybridization does not exist, therefore no illumination source exists, nor a device for capturing the reactions that happen. The hybridization has to be registered visually.

The document DE10161529 describes a bio-sensor for the registration and identification of DNA molecules, with the immobilization of the sample performed by a cavity covered with gold that works as a probe, which contains a photodiode. By illumination of the sample, the optical signals are detected by a photodiode. This invention differs substantially from the proposed present invention especially in respect to the probes connected to the detector and also on the design of the structure. Also the light source cannot illuminate directly the detection unit, which it is different from the present invention.

The document EP0248690 deals with methods and devices for the identification of viral nucleic acids in biological environments. Although it refers to the possibility of using a colorimetric method, it is very different from the present invention by its structure and detection method.

The document CN1661094 relates to a method for gene mutation detection by the combination of: amplification of specific alleles, gold nanoprobes and colorimetric methods. However, the described process differs substantially of the one presented here since it does not specify the detection method of the hybridization. The hybridization will be registered visually. No illumination source exists, nor a device for capturing the reactions that happen.

The document US2006014237 presents a detection system for biological agents by combination of: light emitting diodes for intermittently exposing the samples to electromagnetic radiation, circuitry to provide the exposure and photodetectors for detecting the fluorescent emissions resulting for the exposure to the radiation. The described system differs to the one presented here since it not used for nucleic acids detection, so no hybridization process or metal probes are used and the photodetectors are used for fluorescence detection.

The document US2006028955 presents an optical analyzer for biological, chemical and biochemical samples to measure the level of fat and sugar in blood. The system uses laser diodes and photodetectors enabling the analyzer to perform absorbance measurements analyses. This system differs from the one presented here since it is not used for nucleic acid detection, therefore no use of hybridization techniques nor metal nanoprobes.

Analyses of biological samples, as for instance in the specific case of DNA/RNA and proteins, are used in forensic analysis, clinical diagnosis and laboratorial markets and research. Nowadays, these techniques are used for the diagnosis of infectious diseases, although cancer diagnosis and genetics (research) represent relevant areas of application. The main industries that currently use detection methods of biological samples, as for instance in the specific case of DNA/RNA and proteins are:

Defence Organizations->issues associated to bio-safety have provoked the increase in the search for fast and reliable solutions for DNA/RNA tests, especially in the United States.

Medical institutions->they are used for medical diagnosis, namely for screening of genetic diseases or identification of pathogenic agents.

R&D Organizations->Many molecular tests are done using DNA detection for research purposes.

Health centres and laboratories for screening and analysis of infectious diseases.

World health organization.

Governmental and non-governmental organizations for detection, combat and eradication of pathogenic diseases.

Besides these industries, that already use detection methods of biological samples, as for instance, in the specific case of DNA/RNA and proteins, new segments will also be able to make use of these tests, such as:

Food industry->Quality control of products, through sampling of the products and laboratory analyses.

Pharmaceutical industry, for quantification tests of the drug-delivery action.

Veterinary/Agricultural industry->for the detection of pathogenic agents, namely in the case of the agricultural industry, for the detection of genetically modified organisms.

Tests of biological samples, as for instance, in the specific case of DNA/RNA and proteins are already used in a wide range field of applications, however, due to the associated costs and handling difficulties of the samples, the field of applications is limited.

The present invention has the objective to develop a simple and cheap system that will allow the 'substitution' of any detection system (for instance, a conventional spectrophotometer) by a photodetector of high sensitivity, in a wide range of wavelengths from the infrared to the ultraviolet, capable of supplying a qualitative and quantitative information based on the specific and selective hybridization of probes functionalized with gold nanoparticles, or any other metal, for the detection of biological samples, as for instance, in the specific case of specific sequences of DNA/RNA, in a faster way and, at least, as reliable as the existing methods.

This new method, combining two technologies, can lead to significant reductions in costs and time per analyses of biological samples, as for instance, in the specific case of DNA/RNA and, therefore, allow this type of molecular tests to be accomplished in practically any part of the world.

Besides, it is also possible to have a self-powered version of the all sensor system, for fast test application of the type Yes/No, associating the photodetector to a component operating in the photovoltaic mode, presenting a portability characteristic to the system.

GENERAL DESCRIPTION OF THE INVENTION

The present invention reports an integrated system, with the possibility to be self-powered, for detection and quantification of biological samples, for instance, in the specific case of specific nucleic acids sequences, up to about dozens of fentomoles, making use of metal nanoprobes, preferentially gold.

The detection system is based on the response of an optical sensor system, singular and/or integrated, to a controllable monochromatic light source.

The light source is made of low energy solid state lasers (higher precision on the response), organic or inorganic light emitting diodes, whose wavelength range covers the visible spectrum range (400 to 800 nm), namely the blue, green and red colours. In this last case, the light can be even collimated and/or pulsed.

In any case, it is possible to have an 'integrated illumination power source' highly accurate as far as data quantification is concerned, involving fixed applications.

The emitted light can be focused on the sample, with or without using micro-lenses. In a specific concrete case-where the light bean as a circular shape, the dimensions of the incident light beam,—will be always—below—to 2 mm in diameter, or in the case where a light line is projected,—the width of the line is below 2 mm and the length can go up to 100 mm, function of the size of the integrated sensor system used.

The values for the intensity of the light source are controllable between 0.01 mW/cm$^2$ to 100 mW/cm$^2$.

The light source can or cannot be pulsed in order to eliminate the noise associated to the ambient light. In this case the frequency of the pulsed signal can vary between 10 Hz and 2000 Hz.

The single or integrated photosensor system is based on amorphous, nanocrystalline or microcrystalline silicon thin film technology and its alloys, [14-17] as well as new active ceramic amorphous and not amorphous semiconductors, such as multicomponent oxide of IGZO, IAgZO, SnZIO, GZIO, CuOIZ, GITO, etc, able to optically detect absorbed/emitted light.

This photosensor system detects and quantifies colour changes, associated to a reference (signal of the light source) caused by functionalized nanoprobes with organic samples or aqueous solution of biological composites.

The photosensors to be used are based on single or integrated pi'ii'n and/or MIS structures. [18-22]

For the single sensor structures, they are able to detect the light transmitted (or 'emitted') through the sample, generating an electrical signal, current or voltage, quantifiable, which it is a function of the intensity of the light source used, of the concentration of biological composite to analyze and of the wavelength location of the peak, for the spectral response range of the sensor system.

To optimize the signal/noise ratio, the saturation current of the photosensors should be as small as possible.

The signal measured by the single photosensor systems allows a reliable quantitative and qualitative detection. The reliability and accuracy of the method requires the use of a minimum of ten sensors integrated on the same board, so as to determine reliable control limits for the accomplished set of measurements performed (statistical information).

The single sensor system has the following functional characteristics:

a) Responsivity from 10 to 10$^8$, for illumination levels between 0.01 mW/cm$^2$ to 100 mW/cm$^2$;

b) Signal to noise relationship larger than 3 dB, for superior illumination levels of 0.01 mW/cm$^2$;

c) Response times larger than 50 µs;

d) Saturation currents smaller than 10$^{-7}$ A/cm$^2$;

e) Detectivity (unit cmHz$^{1/2}$/W) higher than $10^{11}$ for the peak of the spectral response;

f) Possibility to shift the peak of the spectral response in a range of 100 nm, by appropriate sensor system bias.

In this sensor system, the peak of the spectral response is adjusted in a wide range (400 to 800 nm) by appropriate selection of the composition of the photosensitive layer or by proper use of tandem structure of the photodiode and in a narrower (100 nm) range, by varying the polarization of the sensor.

The substrate where the sensor or group of sensors are deposited is transparent for the range of wavelengths of interest, being possible to micro-groove it on the opposite side, where the deposit of the sensor take place.

Micro-grooving consists in obtaining cavities of conical form with diameter lower than 3 mm and vertex centred with the geometric centre of the sensor, so that it works as a container of the biological solution. By this way, the optical coupling between the light transmitted through the sample to the sensor is also optimized and the amount of biological composite used in the analysis is substantially reduced.

In the case of using more then one single sensor of pi'ii'n and/or MIS structure, these can be connected, in series or parallel, and the resulting electrical signal, current or voltage, coupled to the conditioning electronics circuit, integrated with the sensor (ASIC Application-Specific Integrated Circuit) or external connected to the sensor.

Besides using single structures, we can use integrated structures, matched for different spectral response peaks—up to a maximum of 4. and with transparent output electrodes, differentiated by different active layers that constitute the stacked sensors. This type of structures allows the control associated to the information of one given colour and determines its incremental variation. In this case, it is possible to organize this structure in integrated linear arrays, for multiple and simultaneous detection, which, besides increasing the reliability, increases the accuracy of the quantified data. This means, the measurements are relative and not absolute, being therefore independent of all and any variation of the photocurrent (photovoltage) due to aging or degradation problems of the sensor.

In the case of the integrated sensor, this is composed of, either by groups of different nanosensors arranged in the linear or matricidal form, or placed in two different boards, one on top of each other and shifted, or if not, produced on the same board, as a tandem structure. As an integrated sensor the possibility arises, or not, of having the appropriate electronics for the signal conditioning embedded.

In each of the circuit boards that contain the photosensors, the spectral response peak is optimized in order to maximize the response signal for a given functionalized sample for the corresponding light source selected. By doing so the quantification process error is reduced.

The wavelength band response range for each sensor integrated in a given circuit board is such that, the intensity of the signal associated to the peak of one of them is at least 10 times larger than the signal detected by other detector.

The integrated sensors can be arranged in linear or matrix form, where each of the sensors occupies a minimum area that can be of about 0.3 mm$^2$, separated by the double of the distance of the incident optical beam size.

The integrated sensors can be arranged as a tandem or stacked structure. In this case the sensor facing the sample to be analysed (front sensor) should have as sensitive layer a material with an optical gap and thickness larger than the other ones of the sensors below it.

The integrated sensors exhibit the same functional characteristics as the single ones.

By appropriate polarization bias it is possible to shift the absorption peak either for single or integrated sensors, in order to obtain the maximum photo-response for a given testing sample (difference between the signal coming from the light source and the signal detected by the functionalized sample).

As photosensors we use semiconductor based devices with pi'ii'n, MIS and other similar structures, with high responsivity in the wavelength range between the 400 nm and the 800 nm, where the letters p and n refer to charge injector/collector contacts; the letter i' is the intrinsic layer based on an alloy containing silicon, and other materials such as carbon; i refers to the photosensitive layer with tuneable spectral response, as a function of its composition. For the MIS structure, M refers to a metal type contact, I refer to a nanolayer composed of a dielectric element, with high insulating properties, and S refers to the photosensitive layer with tuneable absorption peak, as a function of its composition.

The sensors above described use silicon and its alloys as active semiconductor in amorphous, nanocrystalline or microcrystalline structure form, as well as ionic oxides such as IZO, ZGO, IGZO, IAgZO, SnZIO, GZIO, CuOIZ, GISnO to work as electrical contacts highly conductive and transparent [23-25]. and also as an active element of switching keys (thin film transistors) between single or matrix/array integrated sensors [26-28].

The production process of the materials described above is based on chemical, physical or physical-chemical techniques, such as chemical vapour deposition assisted by a radio frequency or ultra-high radio frequency plasma (PECVD Plasma Enhanced Chemical Vapour Deposition); chemical vapour deposition assisted by hot wire (HW-CVD); chemical vapour deposition assisted by ultra-violet light or microwaves; dc or rf sputtering assisted or no, by a magnetic field; sol-gel; spin coating, spray pyrolysis; epitaxial atomic growth; thermal evaporation assisted by hot filament or electron beam; electrochemical growth, ink-jet.

The process temperatures used to fabricate the different components of the single or integrated sensors (from now on, always designated as sensors) vary between 20° C. and 400° C., function of their expected functionality and electrical behaviour.

In accordance to what has been previously described the sensors can be produced in any type of substrate such as cellulosic (paper); polymeric (plastic); glass; ceramic and metal, having maximum dimensions of 10×10 cm.

The signal extraction of these sensors is made using high metallic conductivity films, such as Cr or Ag, or high conductivity transparent oxide films, of crystalline or amorphous structure, like ZGO or IZO.

In sensors with a pi'ii'n structure, the p contact should be sufficiently conductive and exhibiting an optical gap that allows the appropriate matching to the next semi-conductor layer in the structure. Besides, it should have a thickness that allows the proper control of the spectral response towards the wavelength range of 400 nm. On the other hand, the doped n contact should exhibit also similar performances to the ones previously described for the p-type contact, but now, to control the spectral response in the wavelength range close to the near the infrared region (around 800 nm).

In the sensors with a pi'ii'n structure, the I' layer should be made of an alloy (for example: silicon-carbon, if it is intended to optimize the response towards the area of blues or silicon-germanium, if it is intended to optimize the response peak towards the area of the near infrared). The thickness of this layer should be such that it should allow the control of the width of the absorption band.

In the sensors with a pi'ii'n structure the i layer should be made of nano-structured silicon, whose control of the optical gap is made either by increasing the hydrogen content or by the addition of small additives to the deposition process, such as methane or germane. In these conditions it will be possible to control the position of the spectral response peak. The thickness of the layer should, in these conditions, always exceed the previous one.

In the sensors with a pi'ii'n structure, the second i' layer should be made of an alloy (for example: silicon-carbon, if it is intended to optimize the response towards the area of blues or silicon-germanium, if it is intended to optimize the response peak towards the area of the near infrared). The thickness should be such that it allows controlling the width of the absorption band but always smaller than the previous one. By doing so, it will be possible to have structures with a wide or narrow band response range. On the other hand, the fine tuning of the position peak will be made by biasing the structure (direct or inverse).

In the sensors with a pi'ii'n structure, the total thickness of the structure can be as thin as 0.3 micrometers or as thick as 30 micrometers, function of the type of materials used, if it is amorphous or microcrystalline.

In the sensors with a MIS structure, the M layer should be made of a highly conductive metal with a high work function (for example: gold or platinum) and sufficiently thin to be transparent to the light wavelength of interest (typically, thicknesses of the order of nanometers) and at the same time to guarantee the desired rectification effect.

In the sensors with a MIS structure, the I layer should be made of a single or multi-layer dielectric material highly compact and dense and highly electrical resistive, (for instance, silicon dioxide or tantalum dioxide; titanium alumina/oxide) but enough thin to allow the carrier transport process by tunnelling.

In the sensors with a MIS structure, the S layer should be made of a semiconductive alloy, or not (for example: silicon-carbon, if it is intended to optimize the response towards the area of blues or silicon-germanium, if it is intended to optimize the response peak towards the area of the near infrared), which allows the growth of a gradual or abrupt film between two adjacent layers, in terms of optical gap (the I layer and the electrode's 'transparent' contact). The semiconductor thickness should be such that it should allow controlling the width of the absorption band. By doing so, it will be possible to have structures with a wide or narrow range band response. On the other hand, the fine tuning of the position of the peak will be made by biasing the structure (direct or inverse).

In terms of tandem/stacked multilayer sensor systems, they can also contain a pin structure that works as a photovoltaic device, capable of self-powering the system. Its integration (number of interlinked cells in series and their dimension) is made according to the specifications for the intended polarization, highly relevant in portable systems.

Any of the structures previously referred can be encapsulated, as for instance by lamination.

The electrical signal (current or voltage) is processed in a such way that the shown results appear in analogical or digital form, as previously described for the case of the single sensor systems.

For each of the cases previously referred to, the sensors produced have a monotonic variation of current (or voltage), which is able to be fully translated into a polynomial function up to grade 4 and be linearized (or represented by a function of order x, in which x varies between 1 and 0.5) by well defined wavelength ranges.

Whatever the case previously referred, the detection can be done in direct or alternating current modes. In the first case it is necessary to take into account the reference background photo-signal from the environment, while for the second case, this is not needed.

The present invention is related to a system and the process of qualitative and/or quantitative identification detection of a biological sample or aqueous solution of biological composite that when functionalized with metal nanoparticles (for example specific sequences of nucleic acids present in biological samples), changes its own range of absorption/emission as a function of the chemical reactions.

A colour change exists, which it is a macroscopic response of a phenomenon occurring at a nanometer scale. For each of these reactions correspond to different incident light absorption/emission response.

The probe is composed of metal nanoparticles with diameter sizes between 5 and 30 nanometers attached for instance to a known DNA/RNA sequence according to the state of the art [9,11,13] that exhibit a colour depending on the metal composition, size and geometry, such as gold or gold alloys nanoparticles. In the case of gold nano-particles, the colour is red. In this case, the absorption peak is located between 500 and 550 nanometers, according to the surface plasmonic resonance. For other colours, resulting from the use of other metals than gold, the peak of absorption shifts to other wavelengths, ranging from 400 nm to 800 nm, in gaps that can be of around 50 nm wide, for each specific case.

The detection mechanism is based on the optical properties of these functionalized probes since the absorption peak changes as a function of the proximity between particles, ruled for example, by DNA/RNA sequences, by varying the ionic forces of the environment where the nanoparticles are contained.

Thus, when preparing and functionalizing various biological sample probes containing gold nanoparticles and a given DNA/RNA, after the addition of the salt it is possible to observe a colour change in the case of a negative result and a no change in colour in the case of a positive result.

The colour change is a macroscopic response which derives from a phenomenon occurring at a nanometer scale, where the DNA/RNA can react in a complementary or non complementary manner. For each of these reactions, there is a corresponding different incident light absorption response.

The absorption spectrum of the sample composed by the gold nanoparticle probes and the aqueous biological composite solutions, such as DNA/RNA test and salt, representing two absorption maxima with a centred Gaussian function behaviour whose peak is centred between 510 and 540 nanometers, which represents the interaction between the probe and the DNA/RNA in a complementary manner (positive), or centred between 615 and 645 nanometers, which represents non-complementary reactions (negative).

Thereby, the colour of the monochromatic light source to be used has to be chosen in accordance with the functionalized probes and biological sample selected, in a complementary manner. In the case of a red colour sample (peak spectral response around 630 nm), a high level of absorption is obtained in the spectral region associated with green colour, that is, around 525 nm. Therefore, a light source for the region associated to green has to be selected.

The detection response corresponds to the difference between the reference values (light beam projected directly onto the sensor) and the values obtained after the inclusion of the biological liquid functionalized with the nanoparticles. This analogue signal is appropriately processed by the adequate electronics and displayed in an analogue or digital manner.

The electronic conditioning of the signal response involves the use of an electronic comparator circuit, which allows performing the difference between the reference signal and the response signal of the light beam after passing the biological composite functionalized with nanoprobes. The exciting optical signal can be continuous (dc) or pulsed (ac), passes through an electronic narrow band pass band filter and the electronic analogue signal is subsequently amplified and/or converted to another form of analogue signal or digital, according to the desired display format.

The detection system is based on a photo-sensor that measures the light intensity difference of a beam of a monochromatic radiation light after passing through a biological liquid sample, for example a DNA mixed with a nanoprobe in the temperature range from 5 to 45° C.

The resulting signal, due to the correct choice of the calibration and rectification algorithm, is proportional to the biological sample concentration.

For each of the previously referred cases, band pass filters will be used or incorporated, every time that the sensor is intended to be used in non-controlled luminosity environments, when we intend to optimize the minimum resolution of the photo-sensors, specially when continuous exciting light signals are used. In this case the filters should match the light source used.

For each of the previous cases, the electronic signal coming from the photo-sensor or photo-sensors, can be guided via a matrix of thin film transistors based on ionic oxides semiconductor and eventually stored in a shift register.

For each of the previously referred cases, the electronic signal received by the sensor can be compared, acquired, amplified or filtered by electronics external to the sensor or embedded in it. In this last case, comparator circuits and logic gates based on ionic transparent oxides will be used, when processing the signal and during its A/D conversion.

Thereby, the detection system developed, is based on a photo-sensor systems, which measures the intensity difference of a beam of a monochromatic radiation light, after passing through non functionalized and functionalized nanoprobes with a biological liquid sample, for example DNA, in a 5 to 45° C. temperature range.

At the same time the photosensor is connected to an electronics circuit (for example a synchronous amplifier), or integrated with a switch (thin film transistor) and a comparator circuit and thin film amplifier which will allow to obtain the results from the assays, in a singular or sequential manner, either using a discrete or integrated system (linear array of subsequent sensors, with the peak spectral response deviated, according to the range of wavelengths to be analyzed), in qualitative and/or quantitative terms. Also, it has to be pointed out that the measurement performed is relative, and therefore not dependent of any possible degradation of the sensor with time. This increases the data reliability.

The light beam intensity reaching the sensor, in this wavelength region, varies as a function of the interactions with the sample due to the maximum absorption peak of the liquid being the same or near the one of the light beam, derived from the presence of the gold nanoparticles.

The biological liquid is placed on the opposite side of the photosensor to where the deposition of the sensors' layers took place, gaining the advantage of the liquid not being in direct contact with the sensor, but rather being in contact with the free substrate side. This fact permits reusing the photosensor, implying a lower cost on the use of the system. On the other hand, the contact area of the functionalized nanoprobes with the sensor is large enough to allow obtaining rigorous results in a qualitative and quantitative manner, without the need to use large amounts of the assay.

These sensors allow the detection of a colour change associated with a chemical process, generating a quantified electric signal, as a function of:

Wavelength of the light emitted/absorbed by the medium;
Shift on the absorption peak, as a function of the reference signal;
Intensity of the signal emitted/absorbed, as a function of the number of possible fentomoles that can be detected;
Shift of the electronic signal detected (current or voltage) by more than one sensor, placed in multilayer structures or integrated as linear arrays but having different deviated/shifted absorption peaks. In this case, one of the structures shows a wide spectral response and the other (or others), a spectral response of narrow band, which is a function of a group of detection levels to be discriminated;
Frequency response as a function of the bias applied to the sensor;
Peak intensity response of the sensor, controlled, as a function of applied bias voltage.

Using this detector it is expected to obtain the following results:

Increase on the sensitivity (as low as fentomoles of target)
Reduce the quantity of biological liquid need for each test (sample);
Capability of miniaturization;
Re-use of the system (the detection is done on the rear part of the transparent substrate where the photo-sensor is deposited, such that there is no direct contact between the biological compound and the semiconductor material), which is an enormous advantage in relation to all known hybridisation systems in a heterogeneous medium—chips, micro-arrays of integrated sensors, membranes;
Possibility of having a portable and self powered version of the system, for quick testing, such as a YES/NO type (a photovoltaic mode of functioning is embedded within the photo sensor, in cases where the response time is sufficient for the envisaged application);
Self powered system (photovoltaic system/sensor integration);
Re-use capability;
Low cost.

FIGURES DESCRIPTION

FIG. 1—represents a possible configuration of the detection and identification of nucleotide sequences system developed—integration of the chemical process with the photo sensor.

A—Detection system;
B—Detection Mechanism

On the top part of the detection system, a monochromatic radiation light source is mounted (1), as for example a laser, which is mechanically pulsed with the help of a chopper (2), so as to reduce noise and ambient light effects. The photosensor is placed on the bottom part of the structure (3) where the drop containing the biological liquid is placed (5). The photo sensor (6 and 7) is connected to a synchronous amplifier (4), which permits obtaining the results of the assays. The biological liquid (5), probe and sample to test, as for example specific sequences of DNA/RNA, proteins, are placed on the surface of the photosensor (6). This configuration has the advantage of the liquid not being in direct contact with the sensor, but rather in contact with the vitreous transparent substrate, which permits the re-use of the photo sensor. This number (7) corresponds to the structure (layers) from which the sensor is made of.

FIG. 2—represents the layers' structure of the devices presented as photo sensors in FIG. 1 by numbers 6 and 7.

As photo-sensors we use devices based on structures of type pi'ii'n, (FIG. 2a) and MIS (FIG. 2b) deposited on a transparent substrate.

Figure 2A:
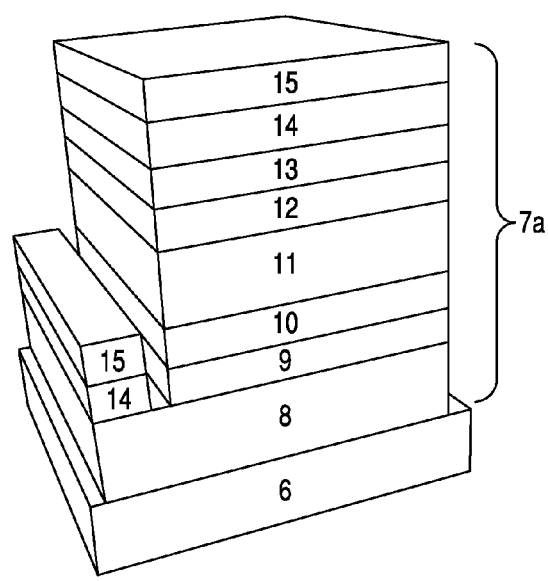

In FIG. 2a) the letters p and n associated respectively with numbers 9 and 13 refer to the charge injector/detector contacts; numbers 10 and 12 correspond to the letter i' and refer to the intrinsic layers obtained from an alloy; 11 corresponds to letter i, and refers to the photo sensitive layer of adjustable spectral response, according to its composition.

Layers 8, 14 and 15 correspond to the photo sensor contacts.

Figure 2B:
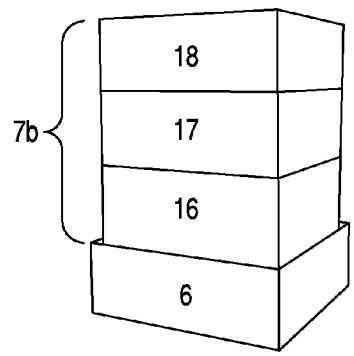

In FIG. 2b on the MIS structures, 16 corresponds to M which refers to a metal type contact, 17 corresponds to I, which refers to a nanolayer formed by a dielectric element, with high isolating properties and 18 corresponds to S, which refers to a photo sensitive layer of adjustable absorption peak, according to its composition.

Figure 3:
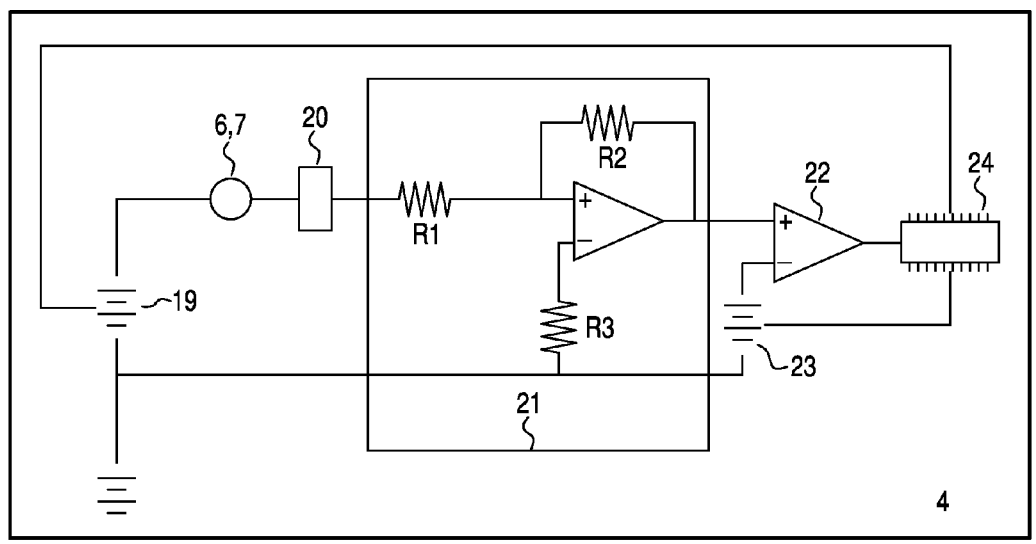

FIG. 3—represents a possible schematic of the simple electronic circuit used for acquisition and processing of the signal coming from the photo sensor, which substitutes the external electronics shown in FIG. 1 by number 4.

Therefore one sensor (6, 7) is connected to a voltage source (19) in order to proceed with its polarization. This source will be controlled by a micro-controller (24) knowing that the sensor polarization to be used depends on the analyses to be performed. A filter (20) exists on the output of the sensor which permits reducing the noise (ambient light) and optimising the minimum resolution for the acquisition of quantitative results. Subsequently, the electric signal is amplified by an amplifier circuit (21) and compared with a comparator circuit (22) to a reference signal (23)—qualitative response, this signal is also controlled by a micro-controller (24), being subsequently sent to the microprocessor for data storage, extra processing and A/D conversion.

In the case of having a circuit composed by an integrated linear array of sensors, a conduction circuit will exist, composed by a switch key (thin film transistor), and directly integrated with the sensor. On top of that, the comparator and amplifier circuit of the signal resulting, can now be integrated within the sensor.

Figure 4:
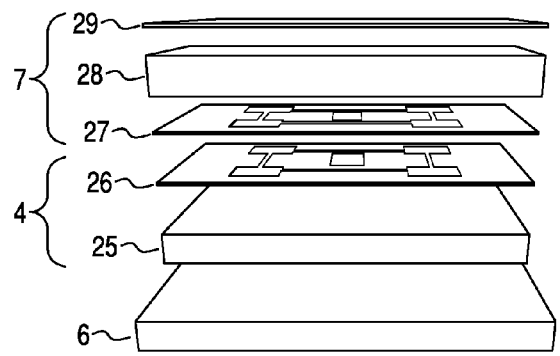

FIG. 4—represents the device structure in an integrated manner, where (6) represents the substrate, as in FIG. 1; (25) the electronics (switching key) based on transparent ionic oxides in order to perform the signal processing, as shown in FIG. 3; (26) an insulating structure; (27) front contact; (28) photo sensor with the structure shown in FIG. 2; (29) rear transparent contact.

DETAILED DESCRIPTION OF THE INVENTION

As previously referred the main components of the system are a monochromatic light source, the described photo sensor and suitable electronics for processing and acquisition of the results.

Subsequently, a detailed description of one possible configuration of the present invention is made, now that various configurations can exist depending on several factors, such as the type of light source (laser or light emitting diodes), type of electronics used for the signal processing, type of photo sensor used (single or integrated), etc.

A single amorphous silicon photo sensor (6 and 7a) is used with a pi'ii'n structure, deposited on a glass substrate, in which the maximum spectral response can be adjusted in a broad range of the visible spectrum such as 530 nm.

The light source (1), is a monochromatic laser of wavelength close to the one above selected, such as 532 nm (green light) and a power such as 5 mW, placed perpendicular to the photosensor (6 and 7a), described previously with a structure such as pi'ii'n structure, so that the incident light points exactly on the geometrical centre of the photosensor (6 and 7a), reducing so the amount of reflected light when it passes through the biological liquid (5). The distance is variable, as a function of the light source power (1), between 5 cm and 30 cm, preferably being 15 cm.

The wavelength of the light source (1), as for instance 532 nm, corresponds to the optimized spectral response peak of the photosensor, and it is selected in a complementary manner according to the metal nanoprobes used, as previously referred to.

Light guiding systems can be used, such as optical fibbers, or lenses, in order to optimize the quantity of the light incident on the sample.

The light source (1), as referred previously is pulsed at a frequency as for instance 130 Hz, in order to eliminate the noise associated with the ambient light, therefore being able to use continuous light sources (1) and to make use of electrical or mechanical pulsing (2) techniques for this incident monochromatic light beam, by using external apparatus (for example a chopper, in order to pulse the signal mechanically).

Also, in order to reduce ambient light effects, optical filters (20) are to be used which are specifically tuned for this light source (1), (e.g., monochromatic laser of wavelength 532 nm) to be used in the essay.

The photosensor (6 and 7) is deposited on the bottom part of the structure (3) and it is optimized for the light source (1) selected to be used on the test being realized. If shifting the peak of the spectral response of the photosensor (6 and 7) to another range is needed, then voltage sources (19) can be used in order to proceed to its polarization and in this way, to shift the spectral response of the photosensor (6 and 7) to the desired range.

This voltage source (19) is manually regulated, since the polarization of the sensor (6, 7) depends on the analyses to be performed.

The biological liquid (5) is placed on the opposite side of the substrate where the photosensor structure was deposited (pi'ii'n structure described previously), gaining the advantage of the liquid not being in direct contact with the sensor, but rather being in contact with the rear side of the substrate that contains the sensor. This fact permits reusing the photosensor, implying a lower cost on the use of the system. On the other hand, the area of contact is large enough to allow rigorous qualitative and quantitative results and so there is no need to use a large quantity of sample, allowing so a cost reduction associated to the sample.

The light source (1), which is located perpendicular to the sensor, will emit a radiation that passes through the biological liquid (5) placed on the surface backside of the substrate that contains the photosensor.

The non absorbed light by the drop of biological liquid (5) passes through the vitreous substrate (6) and it is absorbed by the photosensor, which converts the light signal to a photo-current and/or a photo-voltage (electrical signal).

The electric signal acquired by the photosensor (6 and 7) is compared, subtracted, amplified or filtered by electronic circuits external to the sensor, using synchronous amplifiers (4), regulated to the same frequency as the light source (1), thereby obtaining the results from the electrical signal generated by the photosensor (6 and 7).

The detection response ($R_{DET}$) is measured as a function of the variation of current or voltage of the device, specific for each wavelength and light intensity used, which it is the difference between the reference values, meaning, the value of the reading of the light beam projected directly onto the sensor ($R_{REF}$) and the value of the reading after having placed the biological liquid onto the sensor ($R_{ADN}$).

$$R_{DET} = R_{REF} - R_{ADN}$$

1. Fabrication and Preparation of the Sample:

Various types of biological sample can be used on the system, and therefore the case of nucleic acid (DNA/RNA) identification is pointed out as study case.

The DNA/RNA sample is extracted from blood, saliva, etc., by commonly used processes, for example existing purification kits. Subsequently, the sample is purified, and an amplification step might or might not be necessary. In the case of RNA the amplification step is not necessary.

2. Preparation of the Samples Containing Nanoparticle Probes

The purified DNA/RNA is therefore mixed with nanoparticle probes, where the nanoparticles are made of gold or other metals, in accordance with the following process:

The DNA/RNA, combined with the gold nanoparticle probe, is exposed for 10 minutes to 95° C. in order to denature de double chain and/or secondary structures of the DNA/RNA. Immediately after, the sample is left to cool down for 30 minutes at room temperature allowing the denatured DNA/RNA to hybridize specifically with the gold nanoparticle probe.

An electrolyte (i.e. NaCl) is then added up to a final concentration of 2M.

After 15 minutes at room temperature (between 5 and 45° C.) it is possible to observe the results as a function of the calorimetric change.

3. Results Acquisition

Then, the biological liquid, containing the nucleic acid samples to be detected or identified together with the respective gold nanoparticle probe, is placed on the photosensor backside of the substrate, and the result revealed.

Therefore, when various solutions containing gold nanoparticle probes and DNA/RNA test are being prepared, and after the addition of a salt it is possible to observe the results, as a colour change in the case of being negative or with the colour remaining the same in the case of being positive, which it is characterized by the photosensor having different electrical signals for each case. This corresponds to two different linear behaviours of the photo-sensors, respectively for the colour change (associated to the wavelength) and light intensity change of the light 'emitted' by the nanoprobes.

EXAMPLE

According to what was previously described in the detailed description, the configuration shown in FIG. 1 was chosen for this example.

A single amorphous silicon photosensor was used, deposited on a vitreous substrate (6); the light source (1) chosen was a solid state laser with a wavelength of 530 nm, which is associated to the maximum spectral response of the photosensor [29].

The light source (1) is mechanically pulsed at a frequency of 130 Hz and the photo voltage generated by the photosensor is measured with the help of a synchronous amplifier (4), using the pulsing frequency of the laser as a reference.

The non-absorbed light 'emitted' by the nanoprobes passes through the vitreous substrate (6) and it is absorbed by the photosensor, which converts the signal to a photo-current or photo-voltage.

Since the photosensor works in the photovoltaic mode, no power source is necessary to feed it. The light emitted by the laser works simultaneously to induce variation on the biological liquid absorption, as well as to activate the photo sensor.

The detection response ($R_{DFT}$) was measured as a function of the variation of current of the device, being the difference between the reference values, meaning, the difference value between the reading of the light beam projected directly onto the sensor ($R_{REF}$) and the value of the reading after having placed the biological liquid onto the sensor ($R_{ADN}$).

$$R_{DET} = R_{REF} - R_{ADN}$$

Although the values of the parameters $R_{ADN}$, $R_{REF}$ had been read in the photo-current mode, the obtained results have units of voltage, due to the conversion performed by the synchronous amplifier (4).

The results have a strong linear behaviour as a function of the probe concentration, turning possible to make a proper approach with a correlation factor, for instance better than 0.97.

$$Y(x) = -0.74 + 0.72x$$

This fact satisfies Lambert-Beer's rule, where the increase in probe concentration it translates into an increase of incident light absorption, a fact that maximises the difference of values between $R_{ADN}$ e $R_{REF}$.

The proposed system was effectively applied to DNA detection. The probe was designed to be complementary to a specific genomic region of the RNA polymerase β-subunit of *Mycobacterium tuberculosis* (tuberculosis agent). The results were attained by measuring the responses of the sensor to the colour changes of a blank solution, non-complementary DNA, and complementary DNA.

In this test, four solutions were prepared, keeping the Au-nanoprobe concentration constant at 2.5 nM, namely: buffer solution (solution1), which it is used to prevent major variations on the solution's pH; sample with non-complementary DNA (solution2); samples with complementary DNA from *M. tuberculosis* (solutions 3 and 4).

Results show that all liquids used absorb the incident radiation. This happens since the photosensor used covers the entire visible spectrum region, having its peak optimized for the green region, so even though the colour change implies a difference in absorption of the biological compound, the photo sensor will continue to obtain a signal. Meanwhile, blank and the non-complementary DNA absorbs much less radiation from the light source, allowing a difference in the reading when compared to complementary DNA.

The difference on the reading between solutions 3 and 4 is also a proof that the system allows the quantification of the samples, in accordance to the suitable selection of a calibration algorithm.

In terms of the liquid forming a drop on the surface of the sensor, the influence of the drop effect exists. This physical phenomenon is due both to the refractive index difference between the liquid and the air, and to the geometry of the drop (convex), which acts like a lens.

Despite this, the detected difference between measured values for complementary and non-complementary DNA is significant. This result shows the viability of the method used, since it presents a great sensibility to the measured values, allowing in this way the detection of presence of *M.tuberculosis* DNA, as mentioned in the above example.

References

[1] Videira, Arnaldo, Engenharia Genética - Princípios e Aplicações. LIDEL (2001).

[2] Kirk, B. W., Feinsod, M., Favis, R., Kliman, R. M. & Barany, F., Single nucleotide polymorphism seeking long term association with complex disease. Nucleic Acids Res. 30, 3295-33 11 (2002).

[3] Whelen, A. C. & Persing, D. H., The role of nucleic acid amplification and detection in the clinical microbiology laboratory, Annu. Rev. Microbiol. 50, 349-373 (1996).

[4] Bernard, P. S. & Wittwer, C. T., Real-Time PCR technology for cancer diagnostics. Clin. Chem. 48, 1178-1185 (2002).

[5] Mackay, I. M., Arden , K. E. & Nitsche, A., Real-time PCR in virology. Nucleic Acids Res. 30, 1292-1305 (2002).

[6] Siitari, Haffy. Nucleic acid diagnostics market—Unmet needs and product potential. National Technology Agency, Technology Review 125/2002. Helsinki (2002).

[7] Storhoff, J. J., Lucas, A. D., Garimella, V., Bao, Y. P., Muller, U.R., Homogeneous detection of unamplified genomic DNA sequences based on colorimetric scatter of gold nanoparticle probes. Nat. Biotechnol. 22, 883-887 (2004).

[8] Storhoff, J. J., Marla, S. S., Bao, Y. P., Hagenow, S., Mehta, H., Lucas, A. D., Garimella, V., Patno, T., Buckingham, W., Cork, W., Muller, U. R., Gold nanoparticle-based detection of genomic DNA targets on microarrays using a novel optical detection system. Biosensors and Bioelectronics 19, 875-883 (2004).

[9] Batista, P., Doria, G., Henriques, D., Pereira, E., Franco, R., Colorimetric detection of eukaryotic gene expression with DNA-derivatized gold nanoparticles. Journal of Biotecnology 119, 111-117 (2005).

[10] Cao, Y. C., Jin, R., Thaxton, C. S., Mirkin , C. A. , A two-color-change, nanoparticle-based method for DNA detection. Talanta 67, 449-455 (2005).

[11] Storhoff, J. J., Elghanian, R., Music, R. C., Mirkin, C. A., Letsinger, R. L., One-pot colorimetric differentiation of polynucleotides with single base imperfections using gold nanoparticle probes. J. Am. Chem. Soc. 120, 1959-1964 (1998).

[12] Sato, K., Hosokawa, K., Maeda, M., Rapid aggregation of gold nanoparticles induced by non-cross-linking DNA hybridization. J. Am. Chem. Soc. 125, 8102-8103 (2003).

[13] Lee, P. C., Meisel, D., Adsorption and surface-enhanced Raman of dyes on silver and gold sols. J. Phys. Chem. 86, 339 1-3395 (1982).

[14] R. Martins, H. Águas, I. Ferreira, E. Fortunato S. Lebib, P. Roca i Cabarrocas, L. Guimarães, Polymorphous silicon films deposited at 27.12 MHz, Advanced Materials CVD, 9 (6), 333 (2003).

[15] S. Zhang, L. Pereira, Z. Hu, L. Ranieiro, E. Fortonato, I. Feneira and R. Martins 'Characterization of nanocrystalline silicon carbide films'. Journal of Non-Crystalline Solids, Vol.352. issue1-9, 1410-1415. (2006).

[16] L. Raniero, I. Feffeira, L. Pereira, H. Águas, E. Fortunato and R. Martins 'Study of nanostructured silicon by hydrogen evolution and its application in p-i-n solar cells'. Journal of Non-Crystalline Solids, Vol.352. issue1-9 (2006), 1945-1948 (2006).

[17] I. Ferreira, L. Raniero, E. Fortunato and R. Martins.'Electrical properties of amorphous and nanocrystalline hydrogenated silicon films obtained by impedance spectroscopy'. Thin Solid Films, Vol. 511-512 (2006), pp. 390-393.

[18] S. Zhang, L. Raniero, E. Fortunato, I. Feneira, H. Águas, R. Martins, 'Amorphous silicon-based PINIP structure for color sensor'. Thin Solid Films, 487 (1-2), 268-270 (2005).

[19] L. Raniero, N. Martins, P. Canhola, S. Zhang, S. Pereira, I. Ferreira, E. Fortunato, R. Martins. 'Influence of the layer thickness and hydrogen dilution on electrical properties of large area amorphous silicon p-i-n solar cell', Solar Energy Materials and Solar Cells, 87 (1-4), 349-355 (2005).

[20] Y. Xu, Z. Hu, H. Diao, Y. Cai, S. Zhang, X. Zeng, H. Hao, X. Liao, E. Fortunato and R. Martins 'Heterojunction solar cells with n-type nanocrystalline silicon emitters on p-type c-Si wafers'. Journal of Non-Crystalline Solids, Vol.352. issue 1-9, 1972-1975 (2006).

[21] H. Águas, L. Pereira, D. Costa, E. Fortunato , R. Martins. 'Linearity and sensitivity of MIS Position Sensitive Detectors Using MIS structures'.Journal of Materials Science, 40 (6), (2005), pp. 1377-1381.

[22] E. Fortunato, L. Pereira, H. Águas, I. Ferreira, R. Martins 'Flexible a-Si:H Position Sensitive Detectors', IEEE, 93 (7), 1281-1286 (2005).

[23] A. Pimentel, A. Gonçalves, A. Marques, R. Martins and E. Fortunato 'Role of the thickness on the electrical and optical performances of undoped polycrystalline zinc oxide films used as UV detectors'. Journal of Non-Crystalline Solids, Vol.352, issue 1-9 (2006), pp. 1448-1452.

[24] P. Canhola, N. Martins , L. Raniero, S. Pereira, E. Fortunato, I. Ferreira, R. Martins 'Role of annealing environment on the performances of large area ITO films produced by rf magnetron sputtering'. Thin Solid Films, 487 (1-2) (2005) pp. 27 1-276.

[25] R. Martins, P. Barquinha, A. Pimentel, L. Pereira, and E. Fortunato. 'Transport in high mobility amorphous wide band gap indium zinc oxide films'. Phys. stat. sol. (a) 202. No. 9. (2005), pp. R95- R97.

[26] E. Fortunato, P.M.C. Barquinha, A.C.M.B.G. Pimentel, A.M.F. Gonçalves, A. J. S. Marques, L. M. N. Pereira, R. Martins. 'Fully transparent ZnO thin film transistor produced at room temperature'. Advanced Materials, 17, 5, 590-594 (2005).

[27] E. Fortunato, P. Barquinha, A. Pimentel, A. Gonçalves, A. Marques, L. Pereira, R. Martins. 'Recent advances in ZnO transparent thin film transistors'. Thin Solid Films, 4487 (1-2) (2005) pp. 205-211.

[28] P. Barquinha, A. Pimentel, A. Marques, L. Pereira, R. Martins and E. Fortunato 'Influence of the semiconductor thickness on the electrical properties of transparent TFTs based on indium zinc oxide'. Journal of Non-Crystalline Solids, Vol.352, issue 1-9 (2006), pp. 1749-1752.

[29] L. Raniero, Produção, e Caracterização de Células Fotovoltaicas de Silício Nano-estruturado produzido por plasma de 27.12 MHz, Tese de doutoramento, defendida na UNL, Maio de 2006.

The invention claimed is:

1. A system for detection, identification and quantification of a biological matter, having one or more light sources combined with one or more optical photosensors and various electronic components for obtaining and processing of a signal emitted by nanoprobes, the system comprising:

the one or more light sources being located at a top portion of the system, composed of low energy solid state lasers or light emitting diodes which emit light, wherein the one or more light sources have a wavelength and a controllable luminosity intensity, the wavelength being in a range of between 400 nm and 800 nm and the controllable luminosity intensity ranging between 0.01 mW/cm$^2$ and 100 mW/cm$^2$;

the one or more photosensors, including at least one of amorphous, nanocrystalline and microcrystalline silicon thin films and ceramic semiconductors functioning on a wide range of wavelengths from infrared to ultraviolet, and provide qualitative and quantitative information based on a specific and selective hybridization of probes functionalized with metal nanoparticles; and a power source for the system provided via at least one of a conventional energy source and photovoltaic batteries, wherein the biological matter is not physically fixed to the one or more photosensors and the biological matter is placed on an opposite side of a substrate on which the one or more photosensors are deposited; and wherein the system is configured to transmit light from the one or more light sources through the biological matter and the substrate and then receive the transmitted light with the one or more photosensors, such that the substrate on which the biological matter is to be deposited is located between the one or more light sources and the one or more photosensors, and the one or more photosensors are configured to measure an amount of light absorption by the biological matter.

2. The system for detection, identification and quantification of a biological matter, according to claim 1, wherein the one or more photosensors include a single structure sensible to color and light intensity, the single structure having functional characteristics including a responsiveness between 10 and $10^8$ for the wavelength range, a signal to noise ratio above 3 dB, a time responses higher than 50 μs, and saturation currents of less than $10^{-7}$ A/cm$^2$.

3. The system for detection, identification and quantification of biological matter, according to claim 1, wherein the photosensor is able to produce a monotonic variation of an electrical signal generated from the transmitted light, the electrical signal being proportional to a concentration of the biological matter, when a correct calibration is done and a correction algorithm is selected.

4. The system for detection, identification and quantification of biological matter, according to claim 1, wherein the photosensor is capable of providing energy for auto-polarization of the photosensor.

5. The system for detection, identification and quantification of biological matter, according to claim 1, wherein the substrate is transparent to the wavelength range and the photosensor is micro-machined on an opposite side on which the biological matter is placed.

6. The system for detection, identification and quantification of biological matter, according to claim 1, wherein the photosensors are able to be arranged in at least one of a linear form, as linear arrays of photosensors, a matrix form, and in a tandem configuration.

7. The system for detection, identification and quantification of biological matter, according to claim 6, wherein any of the light sources, the photosensors and electronic switch controllers between arrays of photosensors, are able to be packaged by lamination.

8. The system for detection, identification and quantification of biological matter, according to claim 1, wherein the photosensor is singular or in the multilayer/tandem form and, integrated or not, based on the nanocrystalline silicon and alloys of nanocrystalline silicon.

9. The system for detection, identification and quantification of biological matter, according to claim 8, wherein the photosensor is based on pi'ii'n type structures that include charge injector/detector contacts, an intrinsic layer based on one alloy, and a photosensitive layer of adjustable spectral response, according to a composition of the photosensor.

10. The system for detection, identification and quantification of biological matter, according to claim 8, wherein the photosensor is based on MIS structures, that include a metal type contact, a nanolayer composed of a dielectric element, with high insulating properties and a photosensitive layer of adjustable absorption peak, according to a composition of the photosensor.

11. The system for detection, identification and quantification of biological matter, according to claim 1, wherein the light source is a solid state set, of well defined and extremely narrow radiation spectrum, covering an entire optical spectrum of visible light.

12. The system for detection, identification and quantification of biological matter, according to claim 11, wherein the light source is monochromatic, controllable, and with output powers from 0.01 mW/cm$^2$ to 100 mW/cm$^2$.

13. The system for detection, identification and quantification of biological matter, according to claim 1, further comprises:
   a light source,
   a photosensor connected to a voltage source controlled by a micro-controller,
   a filter,
   an amplifier circuit,
   a comparator circuit, and
   a reference signal generator, connected to the micro-controller and a micro-processor, the reference signal generator being fixed or portable.

14. The system for detection, identification and quantification of biological matter, according to claim 13, wherein:
   the photosensor is connected to a voltage source, in order to proceed to a polarization of the photosensor;
   the voltage source is controlled by the micro-controller;
   the filter existing on an output of the sensor;
   the filter connected to the amplifier circuit;
   the amplifier circuit connected to the comparator circuit which generates a reference qualitative response signal, the reference qualitative response signal also controlled by the micro-controller; and
   the micro-processor is used for data storage, extra processing, and an analog to digital conversion.

15. A process for detection, identification and quantification of biological matter, the process comprising:
   using the system described in claim 1 and metal nanoparticle probes with an integration of at least one of a single and tandem/multilayer sensors based on the silicon thin film technology and alloys of the silicon thin film technology, and a monochromatic and controllable light sources.

16. The process for detection, identification and quantification of biological matter, according to claim 15, further comprising:
   preparing metal nanoparticle probe solutions, preferably gold, of diameter between 5 and 30 nanometers;
   mixing of a nucleic acids sample to be detected and identified with the probe solutions in an interval of temperatures between 5 and 45° C.;
   promoting attachment/aggregation of metal nanoparticle probes to the samples due to a variation of an ionic force in a solution medium; and
   placing resulting solutions, or biological liquid, on a backside surface of the photosensor of the detection system according to claim 15, without having a direct contact between gold nanoparticle probes and the sensor for post hybridization.

17. The process for detection, identification and quantification of biological matter, according to claim 15, wherein the biological matter is genetic material presented in a biological sample.

18. The process for detection, identification and quantification of biological matter, according to claim 15, further comprising:

using a colorimetric method, which detects a color change by a thin film optical sensor, the detection being in accordance with at least one of:

a wavelength of the light emitted and absorbed by a medium;

a wavelength shift, as a function of a reference signal;

an intensity of the transmitted signal emitted and absorbed, as a function of number of fentomoles able to be detected;

a change in an intensity of an electric signal able to be detected in the form of one of a current and a voltage by more than one sensor, arranged in tandem/multilayer configuration where an absorption peak associated with each stacked structure can be shifted;

a frequency response, as a function of a polarization applied to the thin film optical sensor; and a controllable intensity peak response, as a function of an applied polarization voltage.

19. The process for detection, identification and quantification of biological matter, according to claim 15, further comprising:

configuring the system according to claim 15 for at least one of, detection, identification and quantification of samples or solutions of a biological compound to specific DNA/RNA sequences of proteins present in the biological compound.

20. The process for detection, identification and quantification of biological matter, according to claim 1, further comprising:

a chopper for mechanically pulsing the emitted light from the one or more light sources.

* * * * *